(12) United States Patent
Simpson et al.

(10) Patent No.: US 6,730,078 B2
(45) Date of Patent: May 4, 2004

(54) RF ABLATION APPARATUS AND METHOD USING MULTI-FREQUENCY ENERGY DELIVERY

(75) Inventors: John A. Simpson, Carlsbad, CA (US); Veerichetty A. Kadhiresan, Temecula, CA (US); David S. Wood, Temecula, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 52 days.

(21) Appl. No.: 10/127,622

(22) Filed: Apr. 22, 2002

(65) Prior Publication Data

US 2003/0199862 A1 Oct. 23, 2003

(51) Int. Cl.⁷ ............................................. A61B 18/18
(52) U.S. Cl. ........................................ 606/34; 606/41
(58) Field of Search ..................... 606/3.2, 35, 37–42

(56) References Cited

U.S. PATENT DOCUMENTS

| | | | |
|---|---|---|---|
| 4,473,075 A | * | 9/1984 | Rexroth ........................ 606/37 |
| 5,156,151 A | | 10/1992 | Imran |
| 5,372,596 A | | 12/1994 | Klicek et al. |
| 5,383,917 A | | 1/1995 | Desai et al. |
| 5,476,495 A | | 12/1995 | Kordis et al. |
| 5,484,400 A | | 1/1996 | Edwards et al. |
| 5,487,385 A | | 1/1996 | Avitall |
| 5,500,011 A | | 3/1996 | Desai |
| 5,542,916 A | | 8/1996 | Hirsch et al. |
| 5,573,533 A | | 11/1996 | Strul |
| 5,582,609 A | | 12/1996 | Swanson et al. |
| 5,584,830 A | | 12/1996 | Ladd et al. |
| 5,617,854 A | | 4/1997 | Munsif |
| 5,620,481 A | * | 4/1997 | Desai et al. ................ 607/101 |
| 5,637,090 A | | 6/1997 | McGee et al. |
| 5,643,197 A | | 7/1997 | Brucker et al. |
| 5,693,078 A | | 12/1997 | Desai et al. |
| 5,697,909 A | | 12/1997 | Eggers et al. |
| 5,697,928 A | | 12/1997 | Walcott et al. |
| 5,797,903 A | | 8/1998 | Swanson et al. |
| 5,810,802 A | | 9/1998 | Panescu et al. |
| 5,827,273 A | | 10/1998 | Edwards |
| 5,837,001 A | | 11/1998 | Mackey |
| 5,891,136 A | | 4/1999 | McGee et al. |
| 5,971,980 A | | 10/1999 | Sherman |
| 6,001,093 A | | 12/1999 | Swanson et al. |
| 6,024,743 A | | 2/2000 | Edwards |
| 6,036,687 A | * | 3/2000 | Laufer et al. ................ 606/27 |
| 6,050,994 A | | 4/2000 | Sherman |
| 6,059,778 A | | 5/2000 | Sherman |
| 6,171,305 B1 | | 1/2001 | Sherman |
| 6,200,314 B1 | | 3/2001 | Sherman |
| 6,212,426 B1 | * | 4/2001 | Swanson ..................... 600/510 |
| 6,270,493 B1 | * | 8/2001 | Lalonde et al. .............. 606/23 |
| 2003/0073990 A1 | * | 4/2003 | Goble et al. ................ 606/37 |
| 2003/0163123 A1 | * | 8/2003 | Goble et al. ................ 606/34 |

* cited by examiner

Primary Examiner—Michael Peffley
(74) Attorney, Agent, or Firm—Fulwider Patton Lee & Utecht, LLP

(57) ABSTRACT

A first power output with a first frequency is provided to a first set of electrodes while a second power output with a second frequency, different then the first frequency, is provided to a second set of electrodes. Power outputs are provided to electrodes so adjacent electrodes receive power outputs with different frequencies, thereby establishing a voltage potential between adjacent electrodes and bipolar current flow. The frequencies of the power outputs are selected such that the resultant waveform indicative of the magnitude of the amplitude difference between the outputs has a period short enough to avoid stimulation of excitable muscular and cardiac tissue. Periodic frequency switching between the first and second power output provides uniform current flow between the electrodes over a given period of time. The addition of a backplate establishes unipolar current flow.

31 Claims, 8 Drawing Sheets

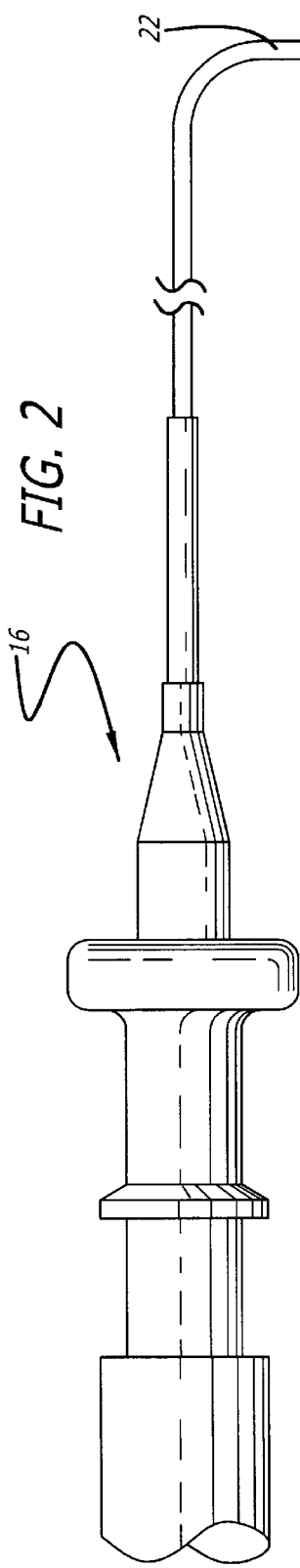
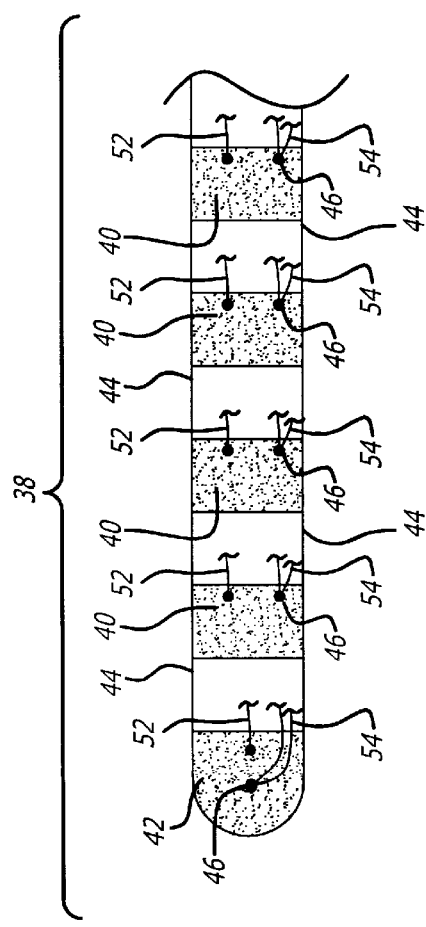

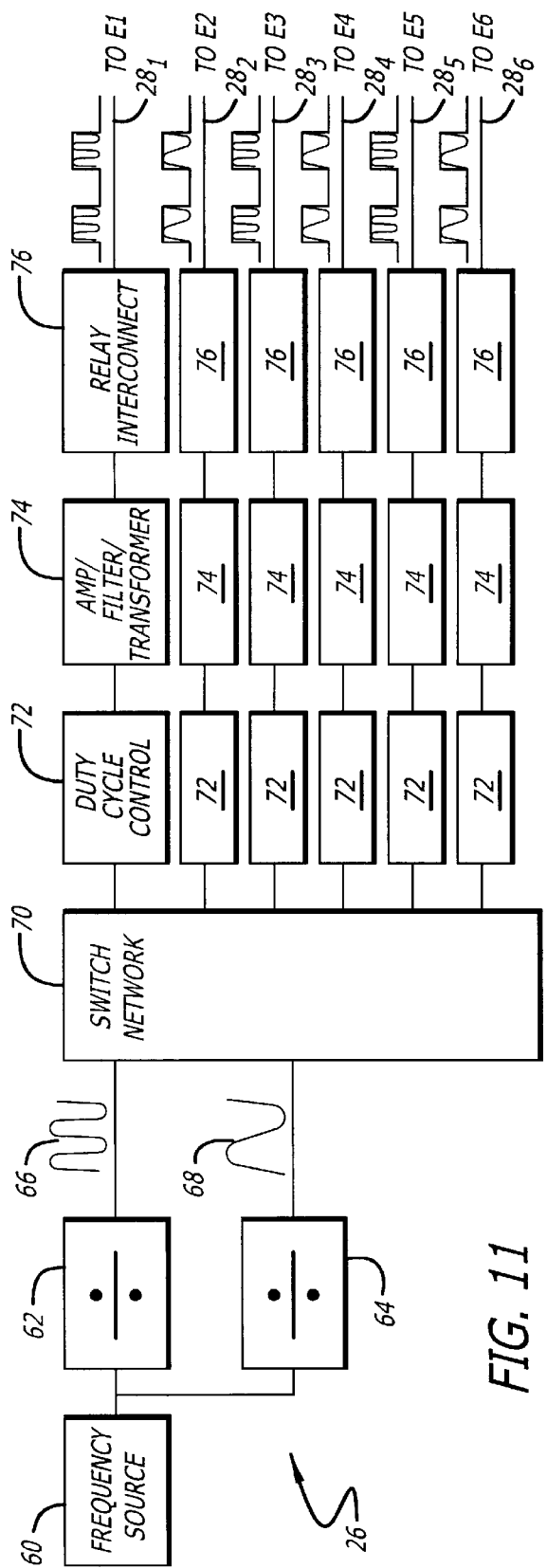
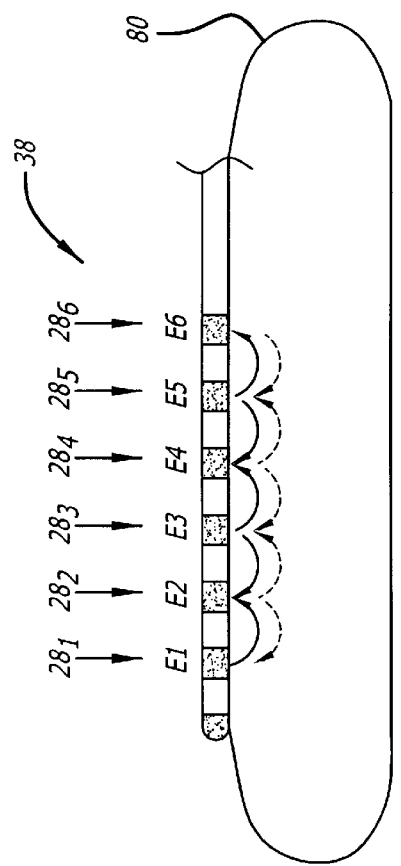
FIG. 11
FIG. 12

RF ABLATION APPARATUS AND METHOD USING MULTI-FREQUENCY ENERGY DELIVERY

BACKGROUND OF THE INVENTION

1. Field of the Invention

The invention relates generally to an electrophysiological ("EP") apparatus and method for providing energy to biological tissue and, more particularly, to a radio frequency ("RF") ablation apparatus for controlling the flow of current through biological tissue so that the depth and continuity of ablation lesions may be controlled.

2. Description of the Related Art

The heart beat in a healthy human is controlled by the sinoatrial node ("SA node") located in the wall of the right atrium. The SA node generates electrical signal potentials that are transmitted through pathways of conductive heart tissue in the atrium to the atrioventricular node ("AV node") which in turn transmits the electrical signals throughout the ventricle by means of the His and Purkinje conductive tissues. Improper growth, remodeling, or damage to the conductive tissue in the heart can interfere with the passage of regular electrical signals from the SA and AV nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, i.e., a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions that prevent atrial reentry and allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In ablation therapy, transmural lesions are formed in the atria to prevent atrial reentry and to allow sinus impulses to activate the entire myocardium. In this sense transmural is meant to include lesions that pass through the atrial wall or ventricle wall from the interior surface (endocardium) to the exterior surface (epicardium).

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In both the unipolar and the bipolar methods, the current traveling between the electrodes of the catheter and between the electrodes and the backplate enters the tissue and induces a temperature rise in the tissue resulting in the creation of ablation lesions.

During ablation, RF energy is applied to the electrodes to raise the temperature of the target tissue to a lethal, non-viable state. In general, the lethal temperature boundary between viable and non-viable tissue is between approximately 45° C. to 55° C. and more specifically, approximately 48° C. Tissue heated to a temperature above 48° C. for several seconds becomes permanently non-viable and defines the ablation volume. Tissue adjacent to the electrodes delivering RF energy is heated by resistive heating which is conducted radially outward from the electrode-tissue interface. The goal is to elevate the tissue temperature, which is generally at 37° C., fairly uniformly to an ablation temperature above 48° C., while keeping both the temperature at the tissue surface and the temperature of the electrode below 100° C. In clinical applications, the target temperature is set below 70° C. to avoid coagulum formation. Lesion size has been demonstrated to be proportional to temperature.

A basic RF ablation system for forming linear lesions includes a catheter carrying a plurality of electrodes, a backplate and an RF generator adapted to provide RF signals to the electrodes to establish bipolar or unipolar current flow. In one such ablation system, as described in U.S. Pat. No. 6,200,314, RF signals having a fixed frequency and amplitude and a controllable phase angle are supplied to each electrode. A backplate is maintained at a reference voltage level in relation to the amplitude of the RF signals. The power control system controls the relative phase angles of the RF signals to establish a voltage potential between the electrodes. Current thus flows between the electrodes and between the electrodes and the backplate to produce linear lesions. In order to establish the phase difference between RF signals, the system requires a programmable logic array and a controllable frequency source. The logic array receives phase control signals from a microprocessor and controls the frequency source accordingly.

In other less complex RF ablation systems, such as those described in U.S. Pat. Nos. 5,810,802 and 6,001,093, a controller electrically couples an indifferent electrode, i.e., backplate, and each of several electrodes to a single RF source through a network of switches. Depending on the setting of its associated switch, an electrode may be set to either an energy emitting polarity, an energy receiving polarity or neither (inactive). Using the switches, the system may be configured so that current flows between the electrodes or between the electrodes and the backplate. The system, however, does not provide for simultaneous unipolar and bipolar operation, thus lesion depth and continuity characteristics may be inadequate.

Hence, those skilled in the art have recognized a need for a multi-channel ablation system having power output control capability for providing periodically fluctuating voltage potentials between electrodes to thereby induce unipolar and bipolar current flow through tissue without reliance on complex phasing circuitry. The invention fulfills these needs and others.

SUMMARY OF THE INVENTION

Briefly, and in general terms, the invention is directed to multi-channel ablation systems having controllable power output capability for providing periodically varying voltage potentials between electrodes to thereby establish unipolar or bipolar current flow through biological tissue.

In one aspect, the invention relates to an ablation system including a catheter having a plurality of electrodes and a power generator. The power generator provides a first power output having a first frequency to at least one electrode defining a first electrode set and a second power output having a second frequency to at least one electrode defining a second electrode set. The first frequency is different then the second frequency. The frequency difference establishes a voltage potential between the electrode sets resulting in bipolar current flow between the electrodes.

In a detailed aspect, the first frequency and the second frequency are such that the voltage difference of the first power output with respect to the second power output yields a resultant waveform having a period no greater than approximately 100 microseconds, to thereby prevent stimulation of excitable muscular and cardiac tissue. In further detailed aspects, exemplary second-frequency-to-first-frequency ratios and resultant waveform periods include 3:1 and 2 microseconds, 2:1 and 2 microseconds, 1.5:1 and 4 microseconds, 1.25:1 and 8 microseconds and 0.5:1 and 4 microseconds. In another detailed facet of the invention, the ablation system includes a processor that periodically switches the first and second power outputs such that during a first time period the first power output is provided to the first electrode set and the second power output is provided to the second electrode set and during a second time period the first power output is provided to the second electrode set and the second power output is provided to the first electrode set.

In another aspect, the invention relates to a system for delivering energy to biological tissue associated with a biological site. The system includes a catheter carrying an electrode system having a plurality of electrodes at its distal end. The electrode system is adapted to be positioned proximal to the biological tissue. The system further includes a backplate that is adapted to be positioned proximal to the biological site so that the biological tissue is interposed between the electrode system and the backplate. Further included in the system is a power control system that provides a first power output having a first frequency to at least one electrode defining a first electrode set and a second power output having a second frequency, different then the first frequency, to at least one electrode defining a second electrode set. The frequency difference provides bipolar current flow between the electrodes. The power control system also establishes a voltage potential between the backplate and at least one of the first and second electrode sets, thereby providing unipolar current flow.

In another facet, the invention relates to a power control system for delivering energy to biological tissue interposed between a plurality of electrodes. The power control system includes a power generator that provides a first power output having a first frequency and a second power output having a second frequency, different then the first frequency. The power control system also includes a processor programmed to control the power generator such that the first power output is provided to at least one electrode defining a first electrode set and the second power output is provided to at least one electrode defining a second electrode set.

In a detailed aspect, the power generator is adapted to provide the first and second power outputs from a single frequency source. In a further detailed aspect, the frequency source provides a power output waveform and the power generator includes at least two frequency dividers. Each divider is adapted to receive the power output waveform and provide the first power output and second power output, respectively. In a still further detailed aspect, the dividers are adapted to provide the first power output and the second power output such that the voltage difference of the first power output with respect to the second power output yields a resultant waveform having a period no greater than approximately 100 microseconds.

In another aspect, the invention is related to a method of delivering energy to biological tissue associated with a biological site. The method includes positioning a catheter having a plurality of electrodes proximal to the biological tissue and providing a first power output having a first frequency to at least one electrode defining a first electrode set and a second power output having a second frequency, different then the first frequency, to at least one electrode defining a second electrode set.

In a detailed facet, the method further includes selecting the first frequency and the second frequency such that the voltage difference of the first power output with respect to the second power output yields a resultant waveform having a period no greater than approximately 100 microseconds. In another detailed aspect, the method also includes periodically switching the first and second power outputs such that during a first time period the first power output is provided to the first electrode set and the second power output is provided to the second electrode set and during a second time period the first power output is provided to the second electrode set and the second power output is provided to the first electrode set. In a further detailed aspect, each of the first and second power outputs has a duty cycle with alternating on and off periods and the periodic switching occurs during the off portion of the duty cycle. In another further detailed aspect, the first frequency and the second frequency are such that the voltage difference of the first power output with respect to the second power output yields a resultant waveform having a period no greater than approximately 100 microseconds and the switching occurs at a time substantially equal to a multiple of the period of the resultant waveform.

These and other aspects and advantages of the invention will become apparent from the following detailed description and the accompanying drawings which illustrate by way of example the features of the invention.

BRIEF DESCRIPTION OF THE DRAWINGS

FIG. 2 is a diagram of the catheter system of FIG. 1 presenting more detail that includes a handle and a catheter shaft having a preformed distal segment carrying an electrode system;

FIG. 3 is a detailed schematic diagram of one configuration of the electrode system of FIG. 2 having a tip electrode and several band electrodes arranged in a linear array;

FIG. 11 depicts a detailed block diagram of one configuration of the multi-power generator of FIG. 5 including a single frequency source, two dividers for providing power output waveforms of different frequencies and a switch network for providing the waveforms to individual output channels;

FIG. 12 depicts the distal segment of the catheter of FIG. 2 positioned against biological tissue and the bipolar current paths through the tissue resulting from the application of the power outputs of FIG. 11 to electrodes E1–E6;

DETAILED DESCRIPTION OF THE PREFERRED EMBODIMENTS

Figure 1:
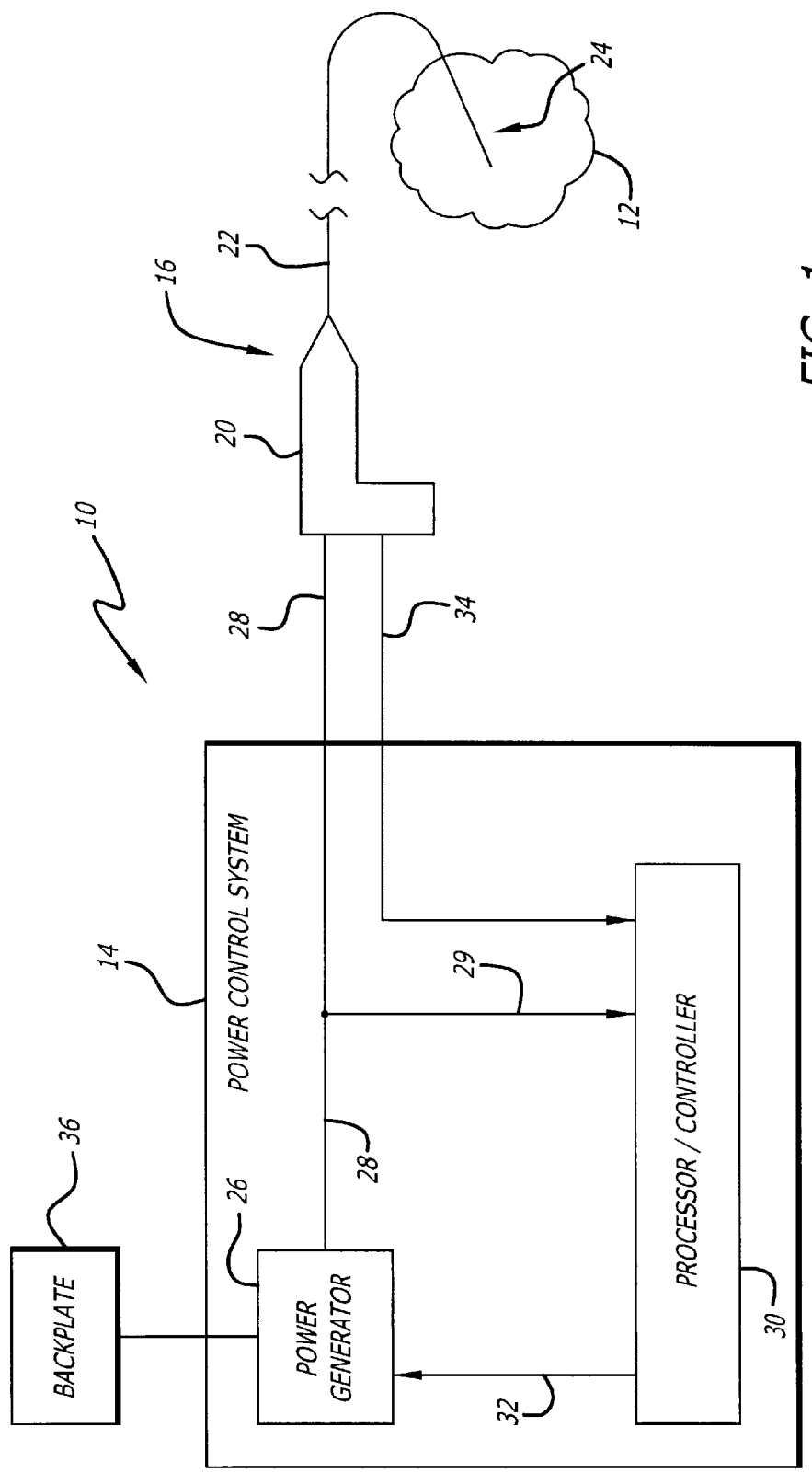
FIG. 1 is a schematic block diagram of an ablation system configured in accordance with aspects of the invention including a power control system ("PCS") and a catheter system.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14 and a catheter system 16. The catheter system 16 includes a handle 20 and a steerable catheter shaft 22 having a distal segment 24. The distal segment 24 carries an electrode system (not shown) and is capable of being percutaneously introduced into a biological site 12.

The power control system 14 includes a power generator 26, through which it provides power 28 to the catheter system 16. Although the power 28 provided by the power generator 26 is illustrated as a single output, the power generator 26 may have any number of channels through which it provides a plurality of power outputs, each characterized by a waveform having an associated amplitude, frequency, phase and duty cycle having alternating instances of peak power, i.e., "on" periods, and very low or zero power, i.e., "off" periods. The operation of the power generator 26 is controlled by a processor/controller 30 which outputs control signals 32 to the power generator 26. The processor/controller 30 monitors the power 28 provided by the power generator 26 along a power monitor line 29. In addition, the processor/controller 30 also receives temperature signals 34 from the catheter system 16. Based on the power 28 and the temperature signals 34, the processor/controller 30 adjusts the operation of the power generator 26.

The system 10 may further include one or more backplates 36 or ground pad electrodes. The backplates 36 or ground pad electrodes are connected to the power generator 26 and generally provide a return path for the power 28 delivered to the biological site 12 through the catheter system 16. Backplates 36 or ground pad electrodes are currently available as self adhesive pads with an electrically conductive gel region and are typically affixed to an exterior surface of the biological subject.

As shown in FIGS. 2 and 3, the distal segment 24 of the catheter system 16 includes an electrode system 38. In FIG. 3, the electrode system 38 is shown in schematic form with the components drawn in more detail to more clearly illustrate the relationship between the components. A preferred embodiment of the electrode system 38 includes twelve band electrodes 40 arranged in a substantially linear array along the distal segment 24 of the catheter shaft 22. The electrode system 38 may include a tip electrode 42. (For clarity of illustration, only six band electrodes 40 are shown in FIG. 2 and only four band electrodes 40 are shown in FIG. 3 although as stated, a preferred embodiment may include many more.) The band electrodes 40 are arranged so that there is an electrically non-conductive space 44 between adjacent electrodes. The electrodes 40 are spaced close enough to each other such that a continuous lesion is formed between adjacent electrodes by the bipolar current flowing between the electrodes. In one configuration of the electrode system 38, the width of the band electrodes 40 is 3 mm and the space 44 between the electrodes is 4 mm. The total length of the electrode system 38, as such, is approximately 8 cm for twelve band electrodes.

Figure 4A:
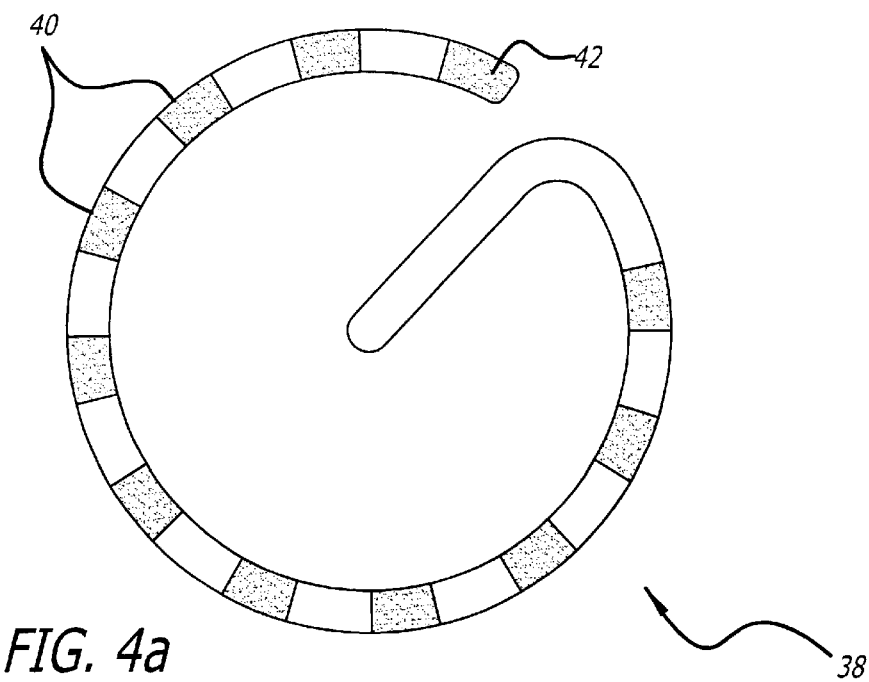
FIG. 4a is a diagram of another configuration of the electrode system of FIG. 2 having a tip electrode and several band electrodes arranged in a circular loop.
Figure 4B:
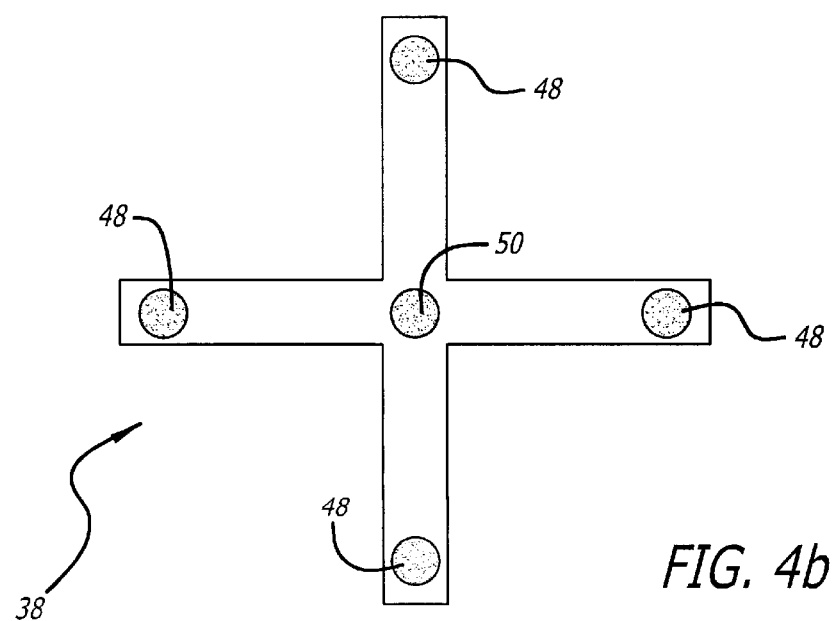
FIG. 4b is a diagram of another configuration of the electrode system of FIG. 2 having a central electrode and four orthogonally arranged branch electrodes.

The arrangement of the electrodes 40, 42 is not limited to a linear array and may take the form of curvilinear arrays or other patterns. For example, as shown in FIG. 4a, the tip electrode 42 and the band electrodes 40 may be arranged in a circular loop. Alternatively, as shown in FIG. 4b, the electrode system 38 may include several branch electrodes 48 orthogonally arranged around a central electrode 50, such as that disclosed in U.S. Pat. No. 5,383,917. A substantially linear or curvilinear array is preferred for certain therapeutic procedures, such as treatment of atrial fibrillation, in which linear lesions of typically 4 to 8 cm in length are desired.

The band electrodes 40 and tip electrode 42 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the electrodes 40, 42 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the electrodes 40 are 7 French (2.3 mm in diameter) with a length of 3 mm and a thickness in the range of about 0.02 mm to about 0.20 mm.

With reference to FIG. 3, associated with the electrode system 38 are thermal sensors 46 for monitoring the temperature of the electrode system 38 at various points along its length. In one embodiment, each electrode 40, 42 has a thermal sensor 46 mounted to it. Each thermal sensor 46 provides a temperature signal 34 (FIG. 1) to the processor/controller 30 which is indicative of the temperature of the respective band electrode 40 (FIGS. 2 and 3) at that sensor. In another embodiment of the electrode system 38 a thermal sensor 46 is mounted on every other band electrode 40. Thus for a catheter having twelve electrodes, there are thermal sensors on six electrodes. In yet another embodiment of the electrode system 38 the odd numbered electrodes have one thermal sensor 46 while the even numbered electrodes have two thermal sensors. In still another embodiment there are two thermal sensors on each electrode. In FIG. 3, which shows an embodiment having one thermal sensor for each electrode, there is shown a single power lead 52 for each electrode 40 to provide power to each electrode for ablation purposes and two temperature leads 54 for each thermal sensor 46 to establish a thermocouple effect. In alternate embodiments, the thermal sensors 46 may include thermistors, resistance temperature detectors (RTD) and fluoroptic probes.

The temperature signals 34 provided by the electrode thermal sensors 46 are used by the processor/controller 30 to monitor the electrodes 40 for unacceptable temperature conditions. Such conditions are described in detail in U.S. application Ser. No. 09/738,032, the disclosure of which is hereby incorporated by reference. For example, in one configuration of the system, if the measured temperature at the interface between the tissue and an electrode 40 is between 5° C. and 9° C. greater than a target temperature programmed in the processor/controller 30, a control signal 32 is sent to the power generator 26 to reduce the duty cycle of the power output 28 being sent to the particular electrode to allow the electrode-tissue interface temperature to cool off. Once the interface is cooled off, the processor/controller 30, may if necessary, incrementally increases the duty cycle of the power output 28, thereby increasing the power to the electrode 40 until the electrode-tissue interface temperature settles to a temperature near the target temperature.

In general, the processor/controller 30 is programmed to control the power such that the closer the electrode-tissue interface temperature is to the target temperature the lesser the rate of change of the duty cycle of the power output 28. For example, if the measured temperature is 20° C. less than the target temperature, the duty cycle maybe set relatively high in order to increase the electrode-tissue interface temperature rapidly. As the measured temperature increases and the difference between it and the target temperature becomes smaller, the duty cycle may be reduced in order to settle in on the target temperature and to avoid exceeding the target temperature by a predetermined amount.

Figure 5:
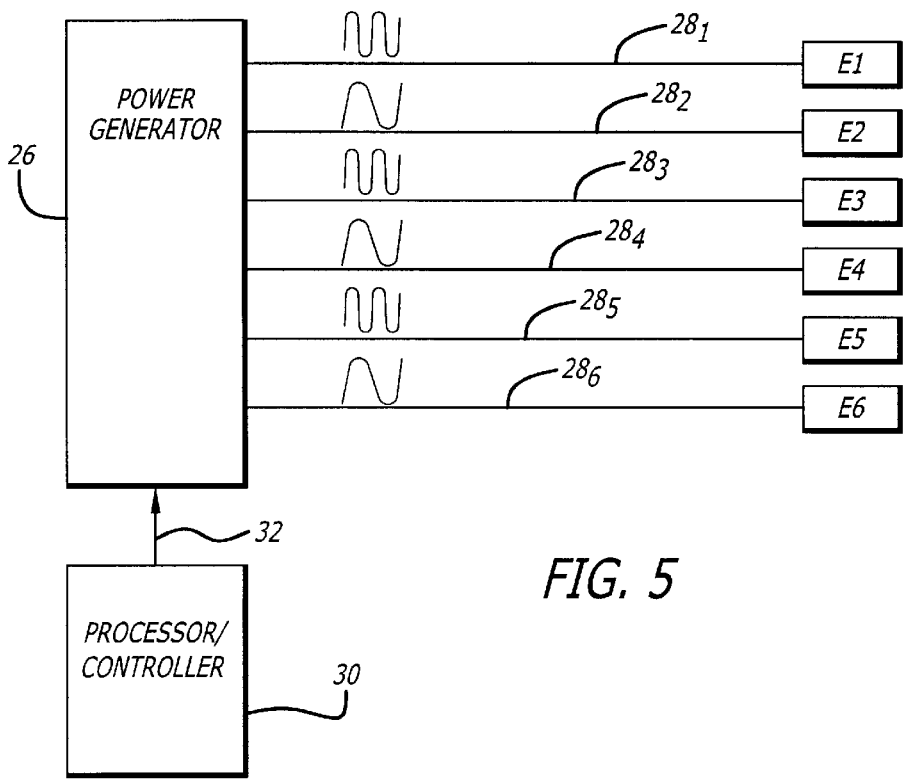
FIG. 5 is a block diagram of one configuration of the power control system of FIG. 1 employing a multi-channel power generator that provides power outputs of two different frequencies.

With reference to FIG. 5, in one configuration of the ablation system, a six-channel power generator 26 is used in conjunction with a catheter system having six ablation electrodes E1–E6. Other configurations of the ablation system may include more or fewer output channels. For example, the ablation system may include a twelve-channel power generator for use with a twelve band electrode catheter.

With continued reference to FIG. 5, the power generator 26 is configured to provide power outputs $28_1$–$28_6$ to the electrodes E1–E6 in a manner that allows for bipolar application of energy through the biological tissue. To this end, a first power output $28_1$ having a first frequency (f1) is provided to a first electrode E1 while a second power output $28_2$ having a second frequency (f2), different then the first frequency, is provided to a second electrode E2. Likewise, third, fourth, fifth and sixth power outputs $28_3$–$28_6$, each having a third frequency (f3), fourth frequency (f4), fifth frequency (f5) and sixth frequency (f6) are provided to third, fourth, fifth and sixth electrodes E3–E6, respectively. The third through sixth frequencies are selected such that adjacent electrodes are driven by signals having different frequencies. Although not shown in FIG. 5, the processor/controller 30 monitors the power output to each electrode and the temperature of each electrode individually through leads 29, 34 as shown in FIG. 1. These leads are not shown in FIG. 5 for clarity of illustration.

In a preferred embodiment, the power outputs $28_1$–$28_6$ may be provided such that frequencies f1, f3 and f5 are substantially equal, thereby forming a first set of power outputs $28_1$, $28_3$, $28_5$, and frequencies f2, f4 and f6 are substantially equal, thereby forming a second set of power outputs $28_2$, $28_4$, $28_6$. Furthermore, the amplitude of each power output $28_1$–$28_6$ is substantially the same. The frequency difference between the first and second sets of power outputs $28_1$–$28_6$ provided to the electrodes E1–E6 establishes an electrical potential between adjacent electrodes thereby establishing bipolar current flow between the electrodes.

Figure 6:
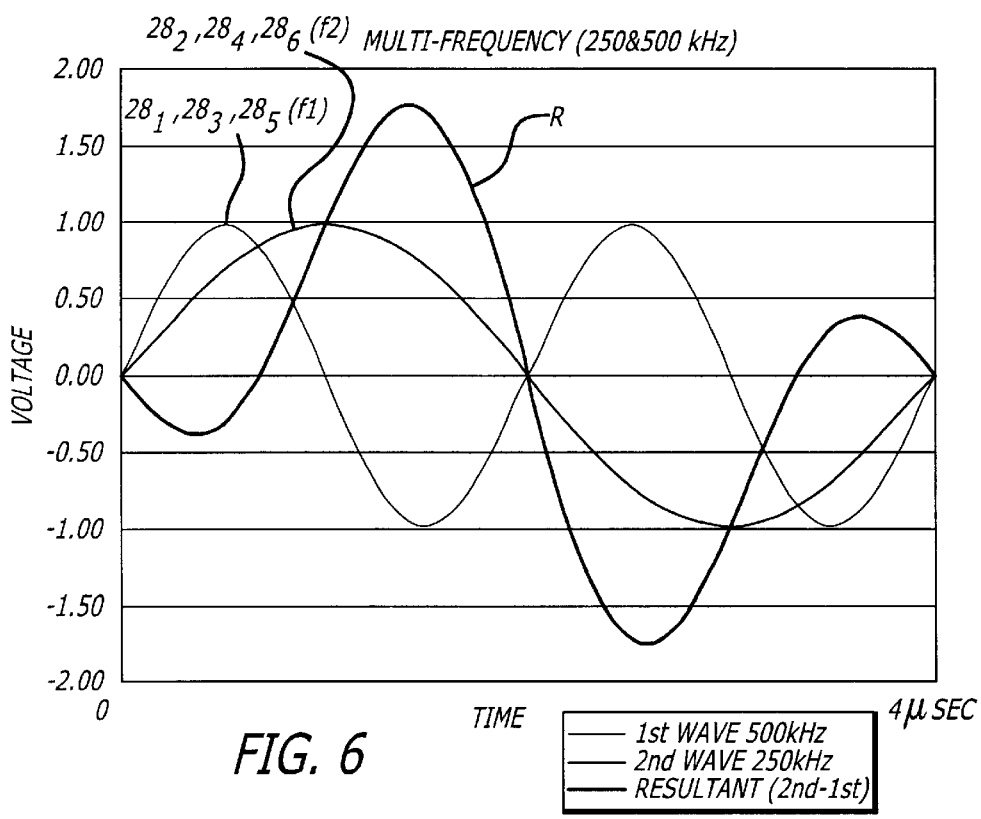
FIGS. 6–10 depict various combinations of power outputs of two different frequencies as a function of time and the resultant waveform indicative of the magnitude of the difference in amplitude between the two outputs.
Figure 7:
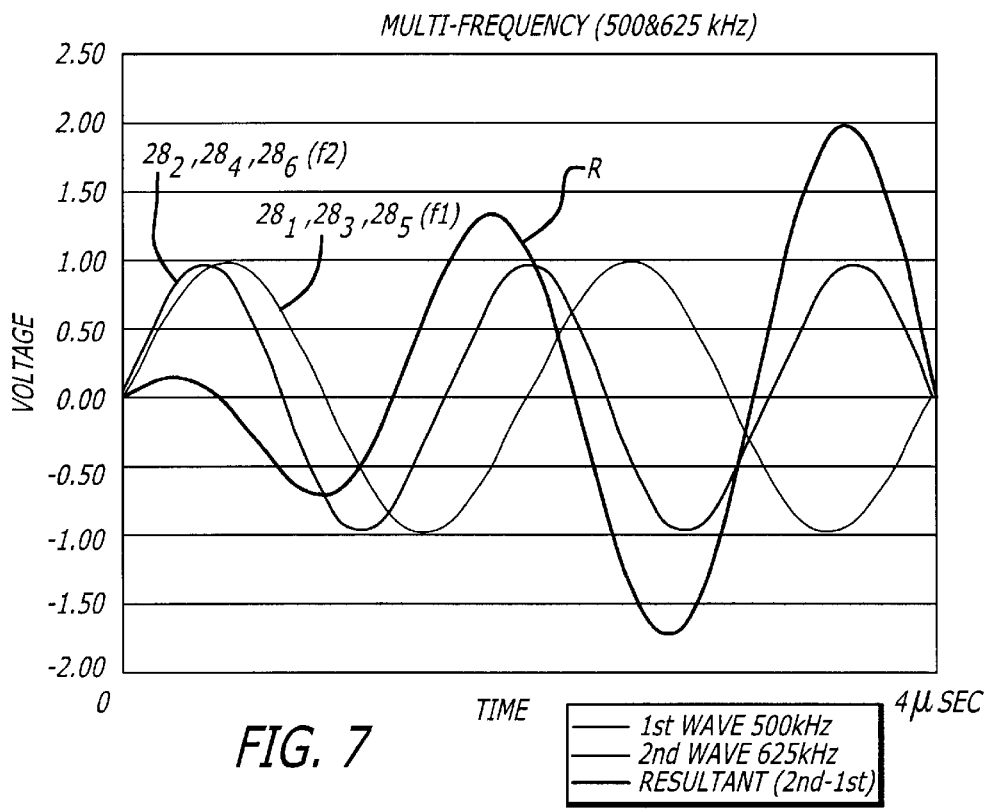
Figure 8:
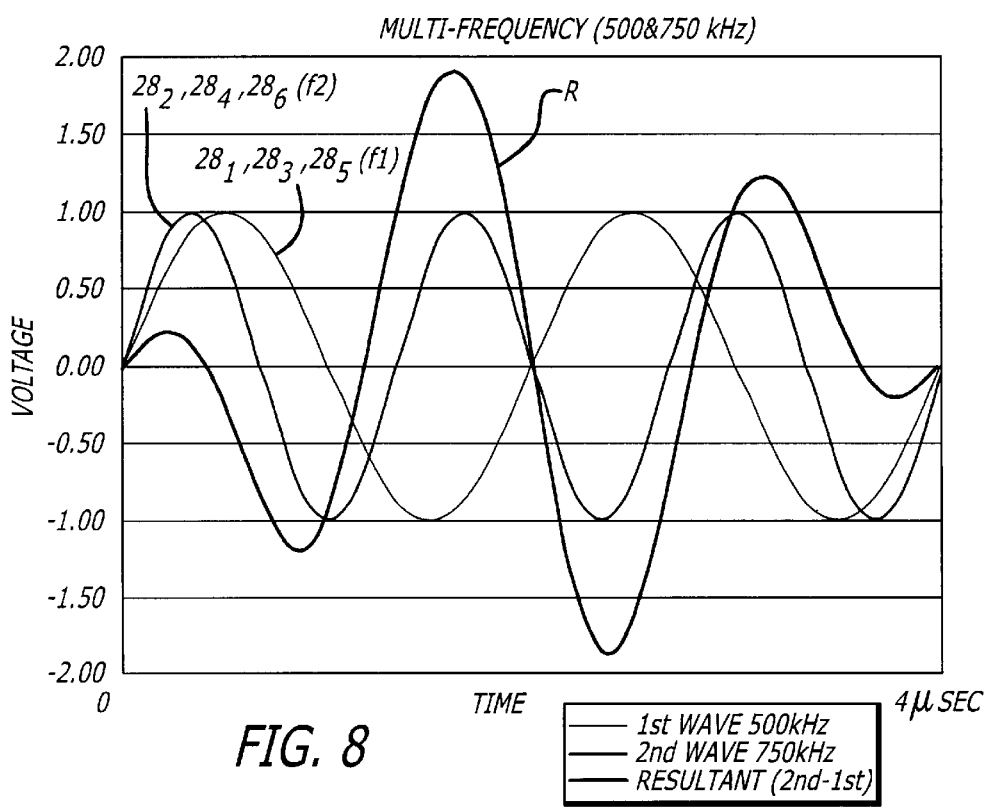
Figure 9:
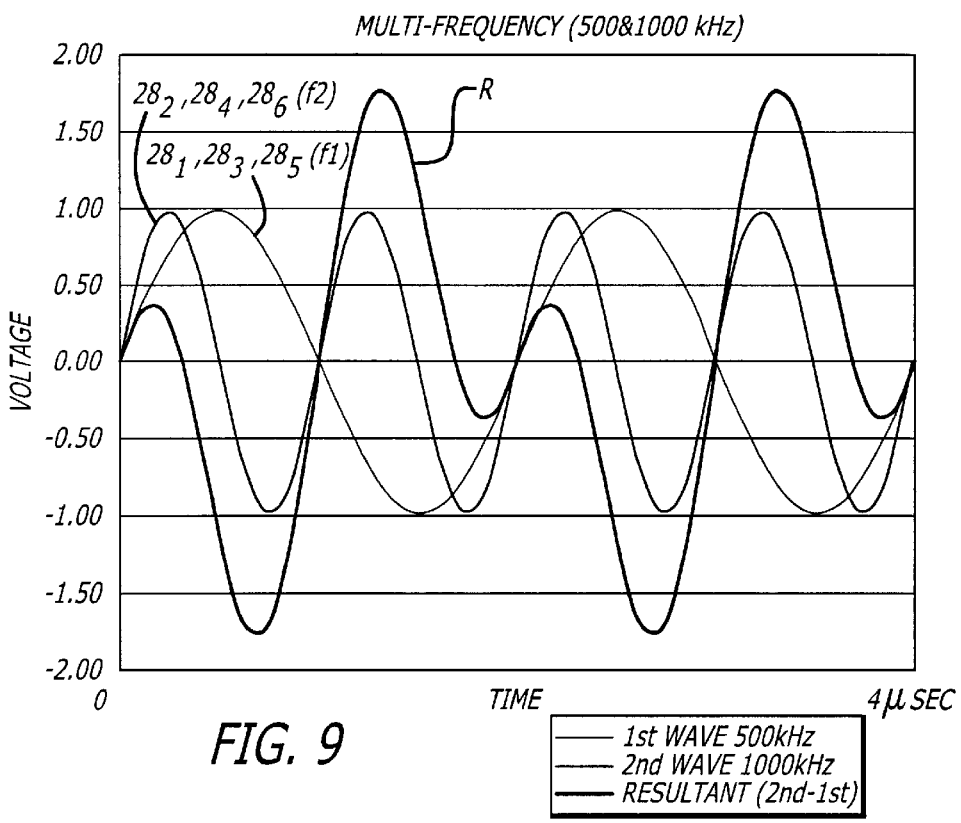
Figure 10:
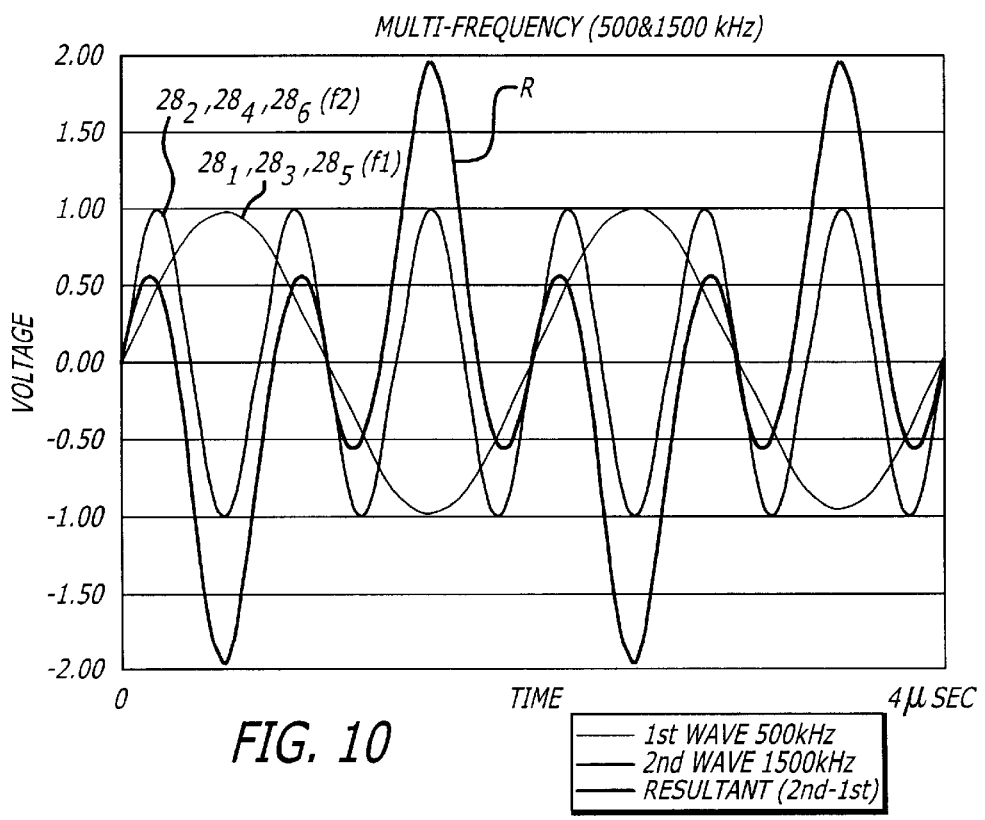

With reference to FIG. 6, the potential difference between the first set of power outputs $28_1$, $28_3$, $28_5$ and the second set of power outputs $28_2$, $28_4$, $28_6$ is shown as a function of time. The resultant waveform R of the potential difference between the two sets of power outputs has a fluctuating amplitude indicative of the fluctuation in the magnitude of the potential difference between the power outputs. It is also noted that, although not sinusoidal, the resultant waveform R is periodic. The period of the resultant waveform R is a function of the frequencies f1, f2, of the two sets of power outputs. The functional relationship between the frequencies may be described in terms of a ratio, e.g., f2:f1.

By proper selection of the frequency ratio, the time required for the resultant waveform R to repeat itself, i.e., its period, can be kept relatively short, e.g., between 2 and 10 microseconds. A short period is desirable in order to avoid cardiac pacing or simulation that occurs when low frequency signals are applied to the heart. Presented in FIGS. 7–10 are several examples of different frequency combinations and their resultant waveforms R. A table summarizing the exemplary frequency combinations is provided below.

| f1 | f2 | f2:f1 | period of waveform R |
|---|---|---|---|
| 500 kHz | 250 kHz | 0.5:1 | 4 microseconds |
| 500 khz | 625 khz | 1.25:1 | 8 microseconds |
| 500 kHz | 750 khz | 1.5:1 | 4 microseconds |
| 500 kHz | 1.0 MHz | 2:1 | 2 microseconds |
| 500 khz | 1.5 MHz | 3:1 | 2 microseconds |

From the table it is noted that simple frequency rations, e.g., 1.5:1, 2:1, 3:1, provide the simplest resultant waveforms with the shortest periods.

To ensure the provision of a resultant waveform R having a short and substantially fixed period (and to thereby avoid the production of low-frequency, pacing signals) it is desirable that the frequency difference between the two sets of power outputs remain substantially constant. With reference to FIG. 11, in order to maintain a substantially fixed frequency difference the power generator 26 may include a single frequency source 60, such as a crystal oscillator. The output of the frequency source 60 is provided to two different divider circuits 62, 64 which generate first and second power output source waveforms 66, 68 having different frequencies. Because power output source waveforms 66, 68 originate from the same frequency source 60 any frequency drift associated with the frequency source produces a corresponding frequency drift in both of the power output source waveforms. Thus the ratio of frequencies among the power output source waveforms remains substantially the same.

With further reference to FIG. 11, the first and second power output source waveforms 66, 68 are input to a switch network 70. In response to control signals (not shown) from the processor/controller, the switch network 70 feeds the first power output source waveform 66, to a first set of power output channels and the second power output source waveform 68 to a second set of power output channels. In a preferred embodiment, the first set of power output channels includes those channels which provide power to the odd numbered electrodes, while the second set of power output channels includes those channels which provide power to the even numbered electrodes. For an electrode system 38 having more electrodes 40 than available power output channels, the electrodes maybe grouped with each electrode in a group having the same power output 28.

Within each power output channel, duty cycle control circuitry 72 controls the duty cycle of the power output waveform 66, 68 in response to control signals (not shown) from the processor/controller. After the duty cycle is set, the power output waveform 66, 68 is output to amplifier/filter/transformer circuitry 74 prior to being provided to its respective electrode through a relay interconnect 76. Exemplary duty cycle control circuitry 72, amplifier/filter/transformer circuitry 74 and relay interconnect circuitry 76 are disclosed in U.S. Pat. No. 6,200,314, the disclosure of which is hereby incorporated by reference.

While the preceding description of one configuration of the power generator 26 includes two dividers for generating two waveforms of difference frequencies, any number of dividers maybe used to generate any number of waveforms. For example, three dividers may be used to generate three waveforms, each having a different frequency. These waveforms may be used to provide first, second and third-frequency power outputs to electrodes E1/E4, E2/E5 and E3/E6 respectively. For a twelve band electrode catheter, the respective waveforms may be applied to electrodes E1/E4/E7/E10, E2/E5/E8/E11 and E3/E6/E9/E12. For ease in describing the features of the system the two-frequency configuration is shown herein.

In a preferred embodiment, the power generator 26 provides individual power outputs $28_1$–$28_6$ to each of the electrodes E1–E6, as such, the bipolar current flow between electrodes may be controlled to obtain lesions of various lengths. For example, with reference to FIG. 12, for an electrode system 38 having six band electrodes E1–E6 positioned proximal to a biological tissue area 80, along linear lesion may be obtained by providing power outputs $28_1$–$28_6$ to the electrodes such that a voltage potential exists between adjacent electrodes. More specifically, a first set of electrodes E1, E3 and E5 maybe provided with a power output $28_1$, $28_3$, $28_5$ having a first frequency f1 such as that shown in FIG. 11 while a second set of electrodes E2, E4 and E6 receive a power output $28_2$, $28_4$, $28_6$ having a second frequency f2 also shown in FIG. 11.

With power output provided in this manner, current flows from the odd electrodes to adjacent even electrodes as indicted by the solid lines, when the voltage of the odd electrode is greater than the voltage of the even electrodes. Likewise, current flows from the even electrodes to the odd electrodes as indicted by the dashed lines when the voltage of the even electrode is greater than the voltage of the odd electrodes. The length of the lesion may be controlled by disconnecting select electrodes E1–E6 from their power outputs through their associated relay interconnect 76. Such disconnection may be done manually through front panel controls on the power control system or automatically by the processor/controller in response to operating conditions, e.g., high electrode-temperature.

The bipolar ablation system thus described is adapted to produce continuous shallow lesions, e.g., approximately 3–4 mm deep. Such lesions may be adequate for procedures within most of the atrium of the heart. However, for procedures within the ventricle, and certain thick areas of the atria, such as the isthmus region, deeper lesions are usually required. In order to produce these lesions both unipolar and bipolar currents are usually required.

Figure 13:
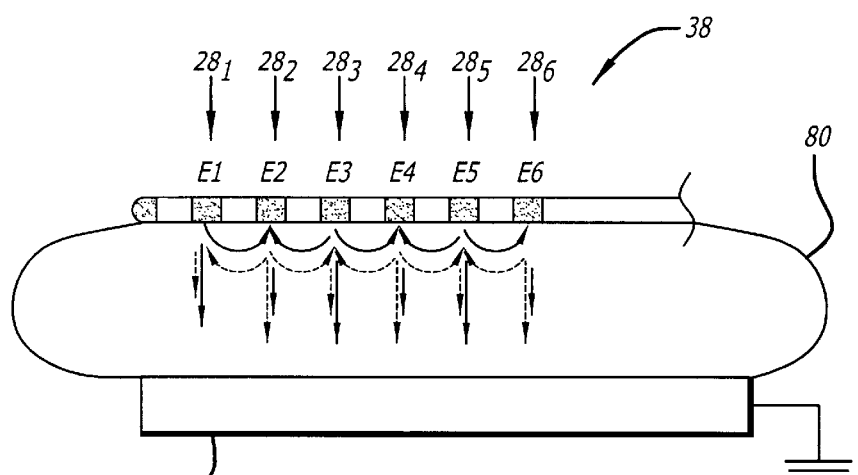
FIG. 13 depicts the distal segment of the catheter of FIG. 2 positioned against biological tissue along with a backplate and the unipolar and bipolar current paths through the tissue resulting from the application of the power outputs of FIG. 14 to electrodes E1, E3 and E5 and the power outputs of FIG. 15 to electrodes E2, E4 and E6.

With reference to FIG. 13, in another ablation system configured in accordance with the invention, a backplate 36 is used in conjunction with the electrode system 38 and the power control system 14 to create unipolar current between the electrode system and the backplate and bipolar current between electrodes 40. In this configuration, the electrode system 38 is positioned proximal to a biological tissue area 80 within a biological site. A backplate 36 is positioned about the biological site such that the biological tissue is interposed between the electrodes E1–E6 and the backplate. The backplate is maintained at a reference voltage different than that of any of the power outputs $28_1$–$28_6$, preferably by connecting the backplate to ground. First and second sets of power outputs $28_1$–$28_6$ similar to those previously described with reference to FIG. 12 are applied to the electrodes such that current flows between adjacent electrodes and between the electrodes and the backplate 36. This current flow is indicated by the solid lines.

It is noted that, due to the frequency difference between the first and second sets of power outputs a greater amount of current may flow from some of the electrodes to the backplate 36 during a given time period. In FIG. 13, this is shown figuratively by the longer solid lines leading from the odd electrodes to the backplate 36. In order to compensate for the possible asymmetry of unipolar current flow the respective frequencies of the first and second sets of power outputs may be switched periodically.

Figure 14:
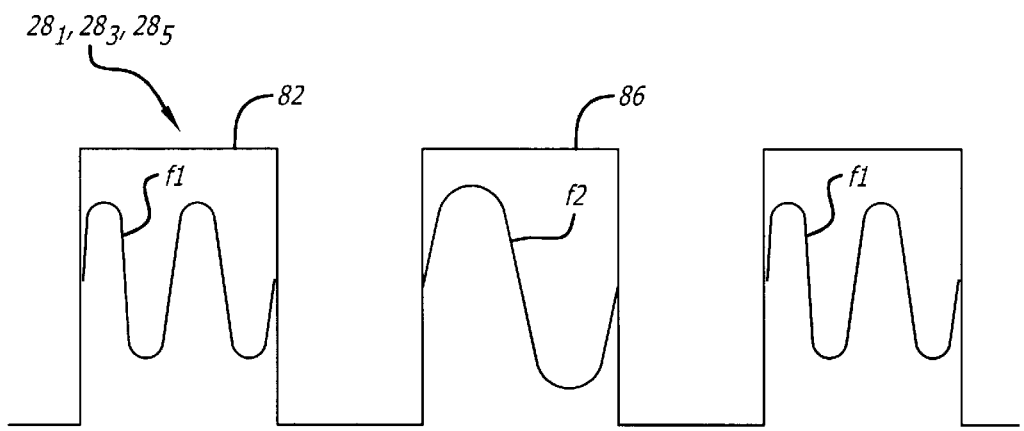
FIGS. 14 and 15 depict first and second duty-cycled power output waveforms respectively, each having alternating on and off periods, with the on periods having alternating high and low frequencies.
Figure 15:
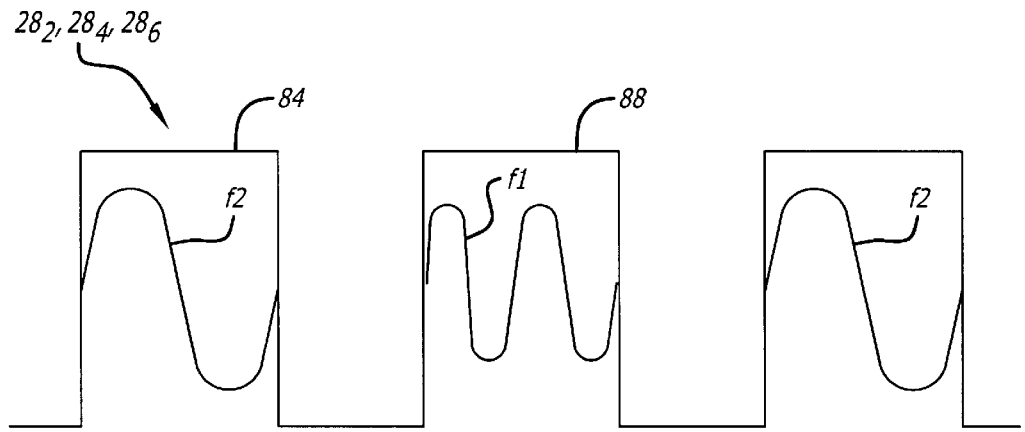

As previously mentioned, the power outputs $28_1$–$28_6$ may have an associated duty cycle with alternating on and off periods. With reference to FIG. 14, during the first on period 82 of their duty cycles, a first set of power outputs $28_1$, $28_3$, $28_5$ are maintained at a substantially constant first frequency f1, while, as shown in FIG. 15, a second set of power outputs $28_2$, $28_4$, $28_6$ are maintained at a substantially constant second frequency f2 which is different then f1 during its first on period 84. During the next on periods 86, 88 of their respective duty cycles, the first set of power outputs $28_1$, $28_3$, $28_5$ are at frequency f2 while the second set of power outputs $28_2$, $28_4$, $28_6$ are at frequency f1. During subsequent on periods, the frequencies of the first and second power outputs change again. Switching the power outputs as such effectively provides each of the electrodes with the same average unipolar current flow over a given period of time. In a preferred embodiment of the invention, switching of power output frequencies occurs during off periods of the duty cycle. In FIGS. 14 and 15, the number of cycles of the sine waves contained within one on period 80, 82, 84, 86 has been substantially reduced in order to emphasize the frequency difference between the power outputs.

The frequency switching described may also be used when the system is operating in a pure bipolar mode to more uniformly distribute the bipolar current flow among the electrodes. More specifically, frequency switching ensures that the amount of bipolar current flowing from, for example E2 to E3 is substantially the same as that which flows from E3 to E2.

With further regard to frequency switching, although the system described has power outputs with associated duty cycles and the switching occurs during the off portion of the duty cycle, a continuous power output may be used. In such a system, the power output switches frequencies, preferably at the end of the resultant waveform R period formed by the power outputs. For example, with reference to FIG. 6, the period of the resultant waveform R is 4 microseconds, accordingly, the switching preferably occurs at a multiple of 4 microseconds, e.g., every 12, 20 or 40 microseconds.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ablation system comprising:
   a catheter having a plurality of electrodes;
   a frequency source providing a signal having a first frequency;
   at least one frequency divider for dividing the signal from the frequency source and providing a signal having a second frequency different than the first frequency;
   a first output channel for providing a first power output having the first frequency to at least one electrode defining a first electrode set; and
   a second output channel for providing a second power output having the second frequency to at least one electrode defining a second electrode set.

2. The ablation system of claim 1 wherein the frequency divider divides the signal from the frequency source so that the first frequency and the second frequency are such that the voltage difference of the first power output with respect to the second power output yields a resultant waveform having a period no greater than approximately 100 microseconds.

3. The ablation system of claim 2 wherein the frequency divider divides the signal from the frequency source so that the ratio of the second frequency to the first frequency is approximately 3:1 and the period of the resultant waveform is approximately 2 microseconds.

4. The ablation system of claim 2 wherein the frequency divider divides the signal from the frequency source so that the ratio of the second frequency to the first frequency is approximately 2:1 and the period of the resultant waveform is approximately 2 microseconds.

5. The ablation system of claim 2 wherein the frequency divider divides the signal from the frequency source so that the ratio of the second frequency to the first frequency is approximately 1.5:1 and the period of the resultant waveform is approximately 4 microseconds.

6. The ablation system of claim 2 wherein the frequency divider divides the signal from the frequency source so that the ratio of the second frequency to the first frequency is approximately 1.25:1 and the period of the resultant waveform is approximately 8 microseconds.

7. The ablation system of claim 2 wherein the frequency divider divides the signal from the frequency source so that the ratio of the second frequency to the first frequency is approximately 0.5:1 and the period of the resultant waveform is approximately 4 microseconds.

8. The ablation system of claim 1 further comprising a processor programmed to periodically switch the first and second power outputs such that during a first time period the first power output is provided to the first electrode set and the second power output is provided to the second electrode set and during a second time period the first power output is provided to the second electrode set and the second power output is provided to the first electrode set.

9. The system of claim 8 wherein each of the first and second power outputs has a duty cycle with alternating on and off periods and the processor is programmed to periodically switch the first and second power outputs during the off portion of the duty cycle.

10. The system of claim 9 wherein the first and second power outputs have approximately the same duty cycle.

11. The system of claim 8 wherein the frequency divider divides the signal from the frequency source so that the first frequency and the second frequency are such that the voltage difference of the first power output with respect to the second power output yields a resultant waveform having a period no greater than approximately 100 microseconds and the processor is programmed to periodically switch the first and second power outputs at a time substantially equal to a multiple of the period of the resultant waveform.

12. The system of claim 1 wherein the first and second power outputs have approximately the same peak-to-peak amplitude.

13. The system of claim 1 wherein the first and second power outputs are in phase.

14. The system of claim 1 wherein the plurality of electrodes are arranged in either of a linear array and curvilinear array and the first electrode set comprises every other electrode and the second electrode set comprises the remaining electrodes.

15. The system of claim 1 wherein the electrodes are arranged in an orthogonal array having a central electrode and a plurality or branch electrodes and the first electrode set comprises the central electrode and the second electrode set comprises the branch electrodes.

16. The system of claim 1 wherein:
   at least one electrode in each electrode set comprises a temperature sensor adapted to provide signals indicative of the temperature at the electrode to the processor; and
   the processor is programmed to convert the temperature signals to a temperature reading, compare the temperature reading to a target temperature and adjust the power outputs based on the difference between the temperature reading and the target temperature.

17. The system of claim 16 wherein each of the first and second power outputs has a duty cycle and the processor is programmed such that when the temperature reading is greater than the target temperature by a predetermined amount, power is reduced by reducing the duty cycle of at least one of the first and second power outputs.

18. The system of claim 16 wherein each of the first and second power outputs has a duty cycle and the processor is programmed such that when the temperature reading is less than the target temperature by a predetermined amount, power is increased by increasing the duty cycle of at least one of the first and second power outputs.

19. A system for delivering energy to biological tissue associated with a biological site, said system comprising:
   a catheter carrying an electrode system having a plurality of electrodes at its distal end, the electrode system adapted to be positioned proximal to the biological tissue;
   a backplate adapted to be positioned proximal to the biological site so that the biological tissue is interposed between the electrode system and the backplate;
   a frequency source providing a signal having a first frequency;
   at least one frequency divider for dividing the signal from the frequency source and providing a signal having a second frequency different then the first frequency;
   a first output channel for providing a first power output having the first frequency;
   a second output channel for providing a second power output having the second frequency; and
   processor programmed to:
      provide the first power output to at least one electrode defining a first electrode set and the second power output to at least one electrode defining a second electrode set, such that a potential difference is established between the first electrode set and the second electrode set; and establish a voltage potential between the backplate and at least one of the first and second electrode sets.

20. The system of claim 19 wherein the frequency divider divides the signal from the frequency source so that the first frequency and the second frequency are such that the voltage difference of the first power output with respect to the second power output yields a resultant waveform having a period no greater than approximately 100 microseconds.

21. The system of claim 19 wherein the processor is programmed to periodically switch the first and second power outputs such that during a first time period the first power output is provided to the first electrode set and the second power output is provided to the second electrode set and during a second time period the first power output is provided to the second electrode set and the second power output is provided to the first electrode set.

22. The system of claim 21 wherein each of the first and second power outputs has a duty cycle with alternating on and off periods and the processor is programmed to periodically switch the first and second power outputs during the off portion of the duty cycle.

23. The system of claim 21 wherein the frequency divider divides the signal from the frequency source so that the first frequency and the second frequency are such that the voltage difference of the first power output with respect to the second power output yields a resultant waveform having a period no greater than approximately 100 microseconds and the processor is programmed to periodically switch the first and second power outputs at a time substantially equal to a multiple of the period of the resultant waveform.

24. A power control system for delivering energy to biological tissue interposed between a plurality of electrodes, said power control system comprising:

a frequency source providing a power output waveform having a first frequency;

at least one frequency divider for dividing the power output waveform from the frequency source and providing a waveform having a second frequency different then the first frequency;

a first output channel for providing a first power output having the first frequency;

a second output channel for providing a second power output having the second frequency; and a processor programmed to control the delivery of the first and second power outputs such that the first power output is provided to at least one electrode defining a first electrode set and the second power output is provided to at least one electrode defining a second electrode set.

25. The power control system of claim 24 comprising at least two frequency dividers, each adapted to receive the power output waveform and provide the first power output and second power output, respectively.

26. The power control system of claim 25 wherein the frequency divider divides the signal from the frequency source so that the first frequency and second frequency are such that the voltage difference of the first power output with respect to the second power output yields a resultant waveform having a period no greater than approximately 100 microseconds.

27. A method of delivering energy to biological tissue associated with a biological site, said method comprising:

positioning a catheter having a plurality of electrodes proximal to the biological tissue;

providing a first power output having a first frequency to at least one electrode defining a first electrode set and a second power output having a second frequency to at least one electrode defining a second electrode set, wherein the first frequency is different then the second frequency.

28. The method of claim 27 further comprising selecting the first frequency and the second frequency such that the voltage difference of the first power output with respect to the second power output yields a resultant waveform having a period no greater than approximately 100 microseconds.

29. The method of claim 27 further comprising periodically switching the first and second power outputs such that during a first time period the first power output is provided to the first electrode set and the second power output is provided to the second electrode set and during a second time period the first power output is provided to the second electrode set and the second power output is provided to the first electrode set.

30. The method of claim 29 wherein each of the first and second power outputs has a duty cycle with alternating on and off periods and the periodic switching occurs during the off portion of the duty cycle.

31. The method of claim 29 wherein the first frequency and the second frequency are such that the voltage difference of the first power output with respect to the second power output yields a resultant waveform having a period no greater than approximately 100 microseconds and the switching occurs at a time substantially equal to a multiple of the period of the resultant waveform.

* * * * *

UNITED STATES PATENT AND TRADEMARK OFFICE
CERTIFICATE OF CORRECTION

PATENT NO. : 6,730,078 B2
DATED : May 4, 2004
INVENTOR(S) : John A. Simpson, Veerichetty A. Kadhiresan and David S. Wood It is certified that error appears in the above-identified patent and that said Letters Patent is hereby corrected as shown below:

<u>Title page,</u>
Item [57], ABSTRACT,
Line 3, delete "then" and insert -- than --.

<u>Column 3,</u>
Lines 10, 45 and 57, delete "then" and insert -- than --.

<u>Column 4,</u>
Line 17, delete "then" and insert -- than --.

<u>Column 7,</u>
Line 20, delete "increases" and insert -- increase --.
Line 50, delete "then" and insert -- than --.
Line 52, delete "283-286" and insert -- $\mathbf{28_3\text{-}28_6}$ --.
Line 63, delete "281-286" and insert -- $\mathbf{28_1\text{-}28_6}$ --.

<u>Column 9,</u>
Line 8, delete "maybe" and insert -- may be --.
Line 22, delete "difference" and insert -- different --.
Line 39, delete "along" and insert -- a long --.
Line 43, delete "maybe" and insert -- may be --.
Line 53, delete "indicted" and insert -- indicated --.

<u>Column 12,</u>
Line 60, delete "then" and insert -- than --.

UNITED STATES PATENT AND TRADEMARK OFFICE
CERTIFICATE OF CORRECTION

PATENT NO. : 6,730,078 B2
DATED : May 4, 2004
INVENTOR(S) : John A. Simpson, Veerichetty A. Kadhiresan and David S. Wood It is certified that error appears in the above-identified patent and that said Letters Patent is hereby corrected as shown below:

Column 13,
Line 43, delete "then" and insert -- than --.

Column 14,
Line 24, delete "then" and insert -- than --.

Signed and Sealed this

Twenty-eighth Day of December, 2004

JON W. DUDAS
*Director of the United States Patent and Trademark Office*